US00PP33706P2

(12) United States Plant Patent
Van Swieten

(10) Patent No.: US PP33,706 P2
(45) Date of Patent: Nov. 30, 2021

(54) ***PHALAENOPSIS* ORCHID PLANT NAMED 'PHALHUSXLA'**

(50) Latin Name: *Phalaenopsis hybrid*
Varietal Denomination: PHALHUSXLA

(71) Applicant: ANTHURA B.V., Bleiswijk (NL)

(72) Inventor: Martinus Nicolaas Gerardus Van Swieten, Utrecht (NL)

(73) Assignee: Anthura B.V., Bleiswijk (NL)

( * ) Notice: Subject to any disclaimer, the term of this patent is extended or adjusted under 35 U.S.C. 154(b) by 0 days.

(21) Appl. No.: 17/300,445

(22) Filed: Jul. 1, 2021

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
CPC ..... A01H 6/62; A01H 5/02
See application file for complete search history.

*Primary Examiner* — Keith O. Robinson
(74) *Attorney, Agent, or Firm* — Jondle & Associates, P.C.

(57) ABSTRACT

A new and distinct variety of *Phalaenopsis* plant named 'PHALHUSXLA', particularly characterized by light greenish-yellow, dotted flowers with reddish-purple, dotted lips, dorsal sepals that are concave in cross section, weak curvature of the lateral lobes of the lip, and is propagated by meristem tissue culture, is disclosed.

3 Drawing Sheets

Genus and species: *Phalaenopsis* hybrid.
Variety denomination: 'PHALHUSXLA'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALHUSXLA'.

The new *Phalaenopsis* plant is a product of a planned breeding program conducted by the inventor in Bleiswijk, the Netherlands. The objective of this breeding program was to create a new *Phalaenopsis* plant with light greenish-yellow, dotted flowers with reddish-purple, dotted lips, suitable for potted plant production.

The new *Phalaenopsis* plant 'PHALHUSXLA' is a result of cross-pollination made by the inventor in September 2011 in Bleiswijk, the Netherlands, of the proprietary female, or seed parent, *Phalaenopsis* hybrid '21864-012' (unpatented) with the proprietary male, or pollen parent, *Phalaenopsis* hybrid '20413-03' (unpatented).

The new *Phalaenopsis* was selected by the inventor as a single plant within the progeny of the stated cross-pollination in a controlled greenhouse in Bleiswijk, the Netherlands, in September 2014. Asexual reproduction of the new *Phalaenopsis* plant by meristem tissue culture since 2015 in Bleiswijk, the Netherlands, has demonstrated that the new variety reproduces true to type with all of the characteristics, as herein described, firmly fixed and retained through successive generations.

Community Plant Variety Rights for this variety have been applied for in the European Union on Sep. 23, 2019 (Application no. 2019/2384), by Applicant who obtained the subject matter disclosed directly from the inventor. 'PHALHUSXLA' has not been made publicly available or sold anywhere in the world prior to the effective filing date of this application with the exception of sales or disclosures made one year or less before the effective filing date of this claimed invention by Applicant who obtained 'PHALHUSXLA' directly from the inventor.

SUMMARY OF THE INVENTION

The following are the most outstanding and distinguishing characteristics of this new cultivar when grown under normal horticultural practices in Bleiswijk, the Netherlands, and can be used to distinguish 'PHALHUSXLA' as a new and distinct variety of *Phalaenopsis* plant:

1) Light greenish-yellow, dotted flowers with reddish-purple, dotted lips;
2) Dorsal sepal shape in cross section is concave; and
3) Curvature of lateral lobe of the lip is weak.

DESCRIPTION OF THE PHOTOGRAPHS

This new *Phalaenopsis* plant is illustrated by the accompanying photographs which show the overall plant habit including blooms, buds, and foliage of the plant; the colors shown are as true as can be reasonably obtained by conventional photographic procedures. The photographs were taken in a greenhouse in Bleiswijk, the Netherlands, from 50-week-old plants in May 2021. Colors in the photographs may differ from the color values cited in the detailed botanical description, which accurately describe the actual colors of the new variety.

DESCRIPTION OF THE NEW VARIETY

Figure 1:
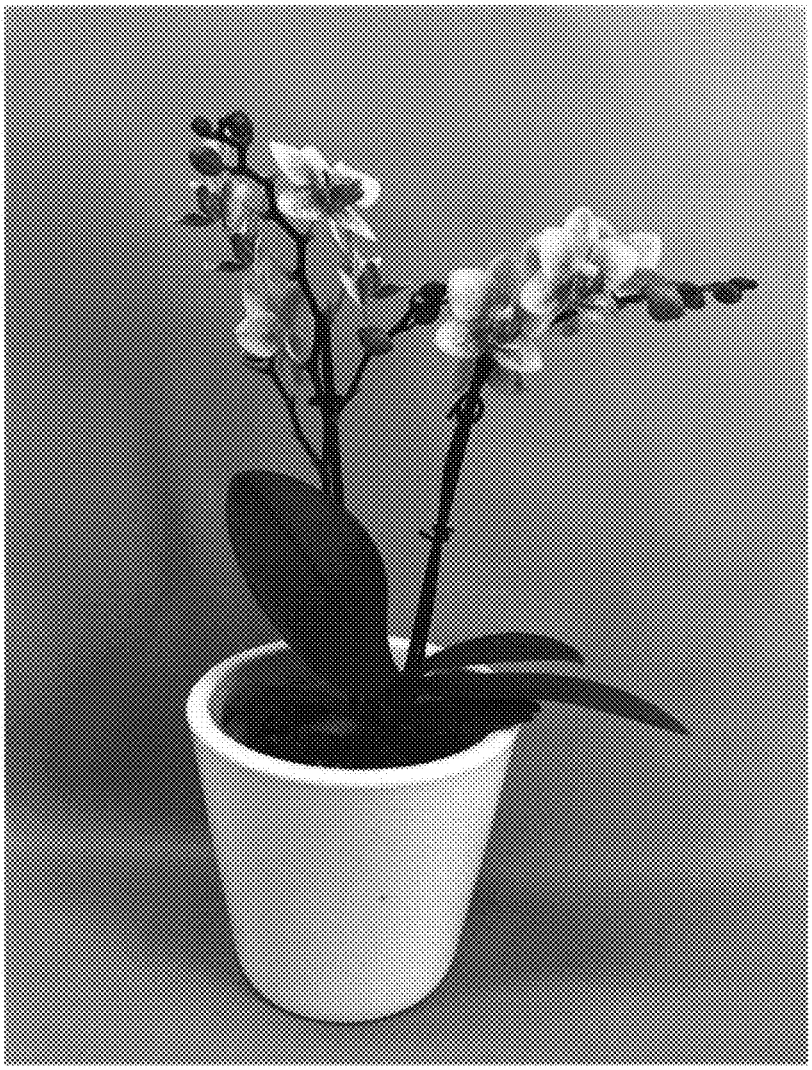
FIG. 1 shows the overall plant habit, including blooms, buds, and foliage of 'PHALHUSXLA'.
Figure 2:
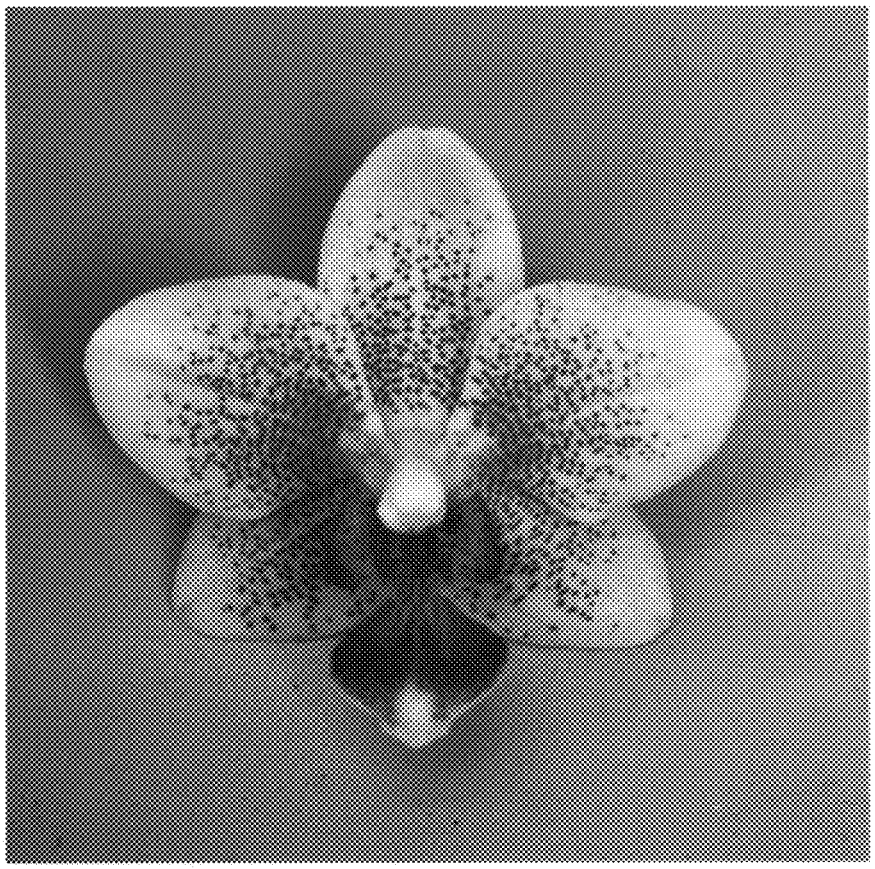
FIG. 2 shows a close-up of a flower of 'PHALHUSXLA'.
Figure 3:
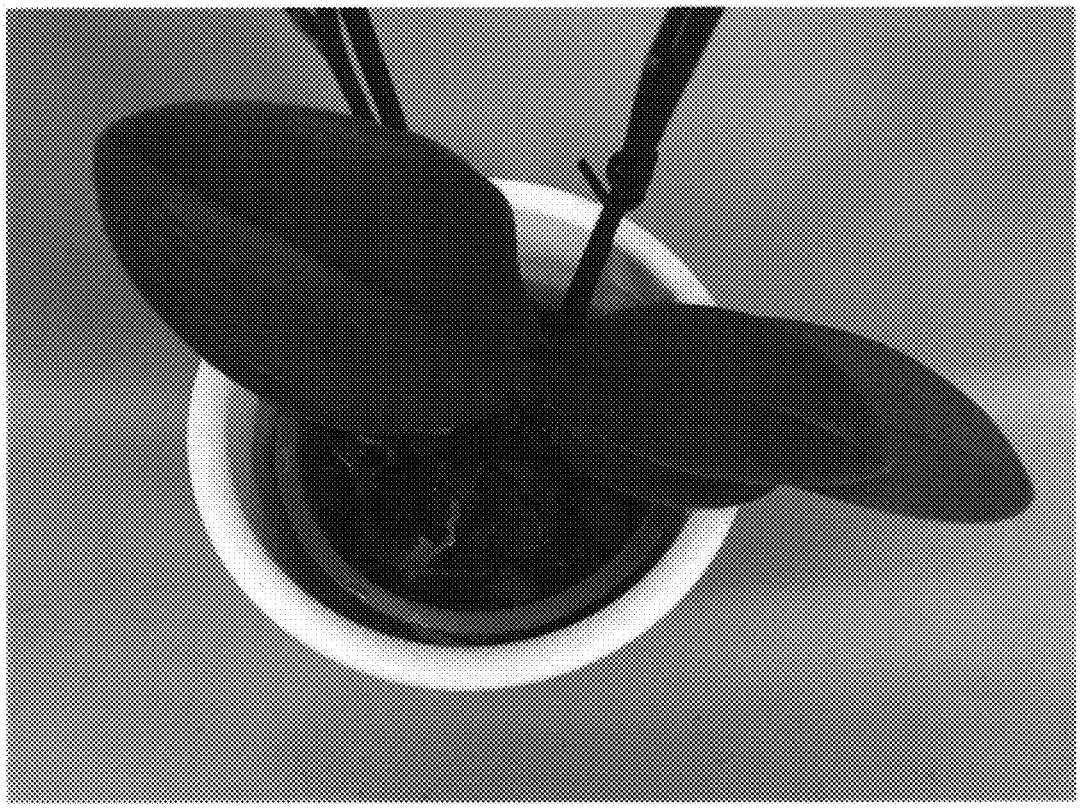
FIG. 3 shows an overhead view of the leaves of 'PHALHUSXLA'.

The following detailed description sets forth the distinctive characteristics of 'PHALHUSXLA'. Plants of the new

*Phalaenopsis* have not been observed under all possible environmental conditions. The phenotype may vary somewhat with variations in environment such as temperature, light intensity, and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, the Netherlands. Observations and measurements were made in May 2021 on flowering plants which were planted in 12-centimeter (diameter) pots. After in vitro propagation, the plants were grown in nursery trays for 20-24 weeks, followed by transplantation to 12-centimeter pots and grown in a greenhouse between 27° C. to 29° C. for 30 weeks, continued by a cooling period of 8 weeks between 18° C. to 20° C. and 12 weeks in a greenhouse of 21° C. Flowering occurs after 50 weeks in 12-centimeter pots.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALHUSXLA'.

Parentage:

*Female parent*.—*Phalaenopsis* cultivar '21864-012' (unpatented).

*Male parent*.—*Phalaenopsis* cultivar '20413-03' (unpatented).

Propagation:

*Type*.—Meristem tissue culture.

Roots:

*Root description*.—Greyed-green (a color in between RHS 190B and RHS 190C) colored roots with branching lateral roots having yellow-green (RHS N144D) colored root tips.

Plant:

*Crop time to flowering*.—Following asexual propagation (in vitro), the rooted cuttings grow for 20-24 weeks. After transplantation into 12-cm pots, the plants are finished after 48 to 50 weeks.

*Growth habit of the peduncle*.—Upright to slightly pendent with raceme and panicle inflorescence.

*Height* (*from soil level to top of inflorescence*).—Approximately 27.0 cm to 32.0 cm.

*Width* (*measured from leaf tips*).—About 23.0 cm to 25.0 cm.

*Vigor*.—Strong.

Leaves:

*Mature leaves*.—Quantity per plant: 7 to 8 leaves are produced before flowering. Length (fully expanded): 11.0 cm to 13.0 cm. Width: 5.5 cm to 6.5 cm. Position of the broadest part of the leaf: At the middle. Shape: Oblong. Base shape: Slightly elongated. Apex: Obtuse unequal. Leaf blade angle with the petiole (measured from the horizontal position): Between 10 degrees and 25 degrees. Leaf margin: Entire. Color: Upper surface: RHS 146A. Lower surface: RHS 146B with a purple overcolor (RHS N77A). Texture (both upper and lower surfaces): Smooth. Thickness: 1.8 mm to 2.3 mm. Variegation: Absent. Venation: Pattern: Parallel. Color of the midvein: Upper surface: RHS N186C. Lower surface: RHS N77A.

Peduncle:

*Quantity per plant*.—1 to 3.

*Number of flowers per peduncle*.—11 to 18.

*Length*.—27.0 cm to 32.0 cm.

*Diameter*.—3.0 mm to 4.0 mm.

*Strength*.—Strong.

*Aspect*.—Upright to slightly pendent.

*Texture*.—Smooth.

*Color*.—Mix of dark reddish-brown (RHS 200A) and yellow-green (RHS 144B).

*Internode length*.—2.0 cm to 3.0 cm.

Inflorescence description:

*Appearance*.—Upright to slightly pendent, raceme and panicle inflorescence with bilaterally symmetrical flowers that open in succession beginning with the lowermost flower.

*Number of inflorescences*.—1 to 2.

*Inflorescence size*.—Height (from base to tip): 130.0 mm to 180.0 mm.

*Flowering time*.—First flowers can be expected 10 to 11 months after planting in a 12-cm pot.

*Flower*.—Height: 40.0 mm to 45.0 mm. Diameter: 48.0 mm to 53.0 mm. Depth of lip: 15.0 mm to 17.0 mm.

*Flower longevity*.—On the plant: 11 to 13 weeks.

*Flower shape*.—Flat.

*Fragrance*.—Absent.

*Flower bud*.—Average size: Medium. Length: 16.0 mm to 18.0 mm. Width: 13.0 mm to 15.0 mm. Shape: Egg shaped. Color: Yellowish-green (RHS N144A); purplish-red diluting stripes (RHS N77B).

*Petals*.—Arrangement: Open/free. Shape: Semi-circular. Apex: Obtuse asymmetric. Margin: Weakly undulated. Length (from base to tip): 22.0 mm to 24.0 mm. Width: 19.0 mm to 21.0 mm. Position of the broadest part of the petal: Toward the base. Color (when fully opened): Upper surface: Basic color: Light greenish-yellow (RHS 3D). Over color: Greenish-yellow margin (RHS 3B) on sides; purplish-red dots (RHS 59B) at the base toward the tip. Lower surface: Basic color: Light greenish-yellow (RHS 3D). Over color: Light purple (RHS 75A) at the base; light greenish-yellow (RHS 3C); light purple midvein (RHS 75B). Number of spots, dots, and stripes on the petals (upper surface): Many dots. Color of spots, dots, and stripes on the petals (upper surface): RHS 59B. Density of netting of the petals (upper surface): None. Color of the netting (upper surface): Not applicable.

*Dorsal sepal*.—Shape: Elliptic. Apex: Emarginated symmetric. Margin: Entire. Length (from base to tip): 24.0 mm to 26.0 mm. Width: 17.0 mm to 19.0 mm. Position of the broadest part of the dorsal sepals: At the middle. Color (when fully opened): Upper surface: Basic color: Light greenish-yellow (RHS 3C). Over color: Purplish-red dots (RHS 59B) at the base toward the tip. Lower surface: Basic color: Light greenish-yellow (RHS 3D). Over color: Very light purple (RHS 75C) at the base; greenish-yellow (RHS 153B) and reddish-purple midvein (RHS N78B) toward the tip. Number of spots, dots, and stripes on the dorsal sepals (upper surface): Medium dots. Color of spots, dots, and stripes on the dorsal sepals (upper surface): RHS 59B. Density of netting of the dorsal sepals (upper surface): None. Color of the netting: Not applicable.

*Lateral sepals*.—Shape: Ovate. Apex: Obtuse symmetric. Margin: Weakly undulated. Length (from base to tip): 23.0 mm to 25.0 mm. Width: 18.0 mm to 20.0 mm. Position of the broadest part of the lateral sepals: At the base. Color (when fully opened): Upper surface: Basic color: Light greenish-yellow (RHS 3C). Over color: Greenish-yellow margins (RHS 3B) on sides; purplish-red dots (RHS 59B) at the base toward the tip. Lower surface: Basic color: Light greenish-yellow (RHS 3C). Over color: Light purple (RHS 75A) at the base; reddish-purple midvein (RHS N78B). Number of spots, dots, and stripes on the lateral sepals (upper surface): Many dots. Color of spots, dots, and stripes on the lateral sepals (upper surface): RHS 59B. Density of netting of the lateral sepals (upper surface): None. Color of the netting (upper surface): Not applicable.

*Labellum* (*lip*).—Whiskers: Present, but very short. Length of whiskers: 1.0 mm to 2.0 mm. Color of whiskers: Yellow (RHS 12A). Pubescence on the lip: Absent.

*Lateral lobe*.—Shape: Type III (as described in the International Union for the Protection of New Varieties of Plants (UPOV) Test Guidelines for *Phalaenopsis*); oblong. Margin: Widely undulated. Length: 11.0 mm to 13.0 mm. Width: 3.0 mm to 5.0 mm. Color: Upper surface: Greenish-yellow (RHS 6C) with a touch of yellow (RHS 14A) at the base; dotted (RHS 187B); light purple (RHS N75B) with purplish-red dots (RHS 70A) toward the tip; dark red margin (RHS 183B) on one side toward the tip. Lower surface: Light yellow-green (RHS 4C); greenish-yellow (RHS 5A) on sides; red margin (RHS 183C) on one side; reddish-purple dots (RHS N78B) toward the tip. Number of spots, dots, and stripes on the lateral lobe: Many dots. Color of spots, dots, and stripes on the lateral lobe: RHS 187B at the base and RHS 70A toward the tip. Density of netting of the lateral lobe: None. Color of the netting: Not applicable.

*Apical lobe*.—Shape: Elliptic. Margin: Entire. Length: 15.0 mm to 17.0 mm. Width: 12.0 mm to 14.0 mm. Color: Upper surface: Greenish-yellow (RHS 6C); dark red dots (RHS 187B and RHS 187C); white (RHS NN155C) with purplish-pink dots (RHS N78C) toward whiskers. Lower surface: Greenish-yellow (RHS 160C); dark red dots (RHS 183B) toward margins; light reddish-purple (RHS N78D) toward whiskers. Number of spots, dots, and stripes on the apical lobe: Many dots. Color of spots, dots, and stripes on the apical lobe: RHS 187B and RHS 187C at the base and RHS N78C toward whiskers. Density of netting of the apical lobe: None. Color of the netting: Not applicable.

*Callus*.—Average size: Small. Height: 3.0 mm to 4.0 mm. Length: 3.0 mm to 4 0 mm. Width: 2.0 mm to 3.0 mm. Color: Yellow (RHS 14A); light greenish-yellow (RHS 5C) on sides; dotted (RHS 183A).

Reproductive organs:

*Column*.—Length: 8.0 mm to 10.0 mm. Diameter: 3.0 mm to 4.0 mm. Color: Light purple (RHS 77D) at the base and white (RHS NN155C) toward tip.

*Pollinia*.—Quantity: 2. Diameter: 0.7 mm to 0.9 mm. Color: Orange-yellow (RHS 23A).

*Ovary*.—Length: 6.0 mm to 8.0 mm. Diameter: 1.2 mm to 1.4 mm.

*Pedicel*.—Length: 23.0 mm to 25.0 mm. Diameter: 1.5 mm to 1.7 mm. Color: Touch of yellow-green (RHS 145B) and lighter yellow-green (RHS 145D) toward the flower. Texture: Smooth.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHALHUSXLA' differs from the female parent plant '21864-012' (unpatented) in that 'PHALHUSXLA' has elliptic apical lobes and columns that are light purple at the base and white toward the tip, whereas '21864-012' has rhombic apical lobes and columns that are white. Additionally, 'PHALHUSXLA' has smaller flowers than '21864-012'.

'PHALHUSXLA' differs from the male parent plant '20413-03' (unpatented) in that 'PHALHUSXLA' has elliptic apical lobes, flowers with a main color of light greenish-yellow, and columns that are light purple at the base and white toward the tip, whereas '20413-03' has ovate apical lobes, flowers with a main color of purple, and columns that are purple. Additionally, 'PHALHUSXLA' has larger flowers than '20413-03'.

'PHALHUSXLA' is most similar to the commercial *Phalaenopsis* plants named 'PHALUSYL' (U.S. Plant Pat. No. 31,166) and 'PHALGITZE' (U.S. Plant Pat. No. 33,274). 'PHALHUSXLA' differs from the commercial variety 'PHALUSYL' in that 'PHALHUSXLA' has obtuse petal apexes, elliptic apical lobes, flowers with a dotted pattern, and calluses with a main color of yellow and light greenish-yellow, whereas 'PHALUSYL' has rounded petal apexes, obtrullate apical lobes, flowers with a spotted pattern, and calluses with a main color of dark reddish-orange.

'PHALHUSXLA' differs from the commercial variety 'PHALGITZE' in that 'PHALHUSXLA' has flowers with a dotted pattern, whereas 'PHALGITZE' has flowers with a striped pattern. Additionally, 'PHALHUSXLA' has a smaller lip depth than 'PHALGITZE'.

I claim:

1. A new and distinct variety of *Phalaenopsis* plant named 'PHALHUSXLA', substantially as described and illustrated herein.

* * * * *